(12) United States Patent
Hohmann et al.

(10) Patent No.: US 6,656,721 B1
(45) Date of Patent: Dec. 2, 2003

(54) **POLYNUCLEOTIDE PORTIONS OF THE BIOTIN OPERON FROM *B. SUBTILIS* FOR USE IN ENHANCED FERMENTATION**

(75) Inventors: Hans-Peter Hohmann, Upper Montclair, NJ (US); Nigel John Mouncey, Verona, NJ (US); Heinrich Winfred Schlieker, Bloomfield, NJ (US); Jeffrey W. Stebbins, Nutley, NJ (US)

(73) Assignee: Roche Vitamins, Inc., Parsippany, NJ (US)

(*) Notice: Subject to any disclaimer, the term of this patent is extended or adjusted under 35 U.S.C. 154(b) by 0 days.

(21) Appl. No.: 09/633,927

(22) Filed: Aug. 8, 2000

(51) Int. Cl.$^7$ ................................................. C12N 1/20
(52) U.S. Cl. ............................. 435/252.3; 435/252.31; 435/254.11; 435/325; 435/419; 435/320.1; 536/23.1; 536/23.2
(58) Field of Search .............................. 536/23.1, 23.2; 435/252.31, 254.11, 419, 325, 471, 320.1

(56) References Cited

U.S. PATENT DOCUMENTS

| 5,773,267 A | 6/1998 | Jacobs et al. |
| 5,837,528 A | 11/1998 | Perkins et al. |

FOREIGN PATENT DOCUMENTS

| EP | 0 730 034 A1 | 9/1996 |
| GB | 952091 | 3/1964 |
| WO | WO 88/09822 | 12/1988 |
| WO | WO 91/11523 | 8/1991 |

OTHER PUBLICATIONS

Perlman, et al., "Fermentation," *Ind. Eng. Chem.*, pp. 1996–2001 (1952).

Mack, et al., "Regulation of Riboflavin Biosynthesis in *Bacillus subtilis* Is Affected by the Activity of the Flavokinase/Flavin Adenine Dinucleotide Synthetase Encoded byribC," *J. Bact.*, vol. 180, No. 4, pp. 950–955 (1998).

Perkins, et al., "Genetic engineering of *Bacillus subtilis* for the commercial production of riboflavin," *J. Ind. Microbiol. Biotechnol.*, vol. 22, pp. 8–18 (1999).

Saito, et al., "Mapping of Genes Determining Nonpermissiveness and Host–Specific Restriction to Bacteriophages in *Bacillus subtilis* Marburg," *Molec. gen. Genet.*, vol. 170, pp. 117–122 (1979).

Itaya, et al., "A neomycin resistance gene cassette selectable in a single copy state in the *Bacillus subtilis* chromosome," *Nucleic Acids Res.*, vol. 17, No. 11, pp. 4410 (1989).

Dev, et al., "Regulation of Synthesis of Serine Hydroxymethyltransferase in Chemostat Cultures of *Escherichia coli*," *Journal of Biological Chemistry*, vol. 269, No. 13, pp. 8394–8401 (1984).

Kiss, et al., "Culture Instability of Auxotrophic Amino Acid Producers," *Biotechnology and Bioengineering*, vol. 40, pp. 75–85 (1992).

Krämer, "Genetic and Physiological Approaches for the Production of Amino Acids," *Journal of Biotechnology*, vol. 45, pp. 1–21 (1996).

Li et al. Generation of Auxotrophic Mutants of *Enterococcus faecalis*. J. Bacteriol. (1995) 177(23):6866–6873.*

Bower et al. Cloning, Sequencing, and Characterization of the *Bacillus subtilis* Biotin Biosynthetic Operon. J. Bacteriol. (1996) 178(14):4122–4130.*

* cited by examiner

Primary Examiner—Ponnathapu Achutamurthy
Assistant Examiner—Kathleen M Kerr
(74) Attorney, Agent, or Firm—Bryan Cave LLP

(57) ABSTRACT

The present invention provides a process for producing a target fermentation product. This process includes providing a fermentation medium containing a recombinantly-produced microorganism that over-produces a fermentation product and contains a mutation which causes auxotrophic growth of the microorganism wherein the auxotrophy within the microorganism does not compromise the ability of the microorganism to produce the fermentation product. The medium is then supplied in excess with all substrates required for production of the fermentation product and in growth limiting amounts with a substrate complementing the auxotrophy. Host cells, vectors, and polynucleotide sequences used in the process are also provided. The polynucleotide sequences of the present invention include sequences derived from the biotin operon of *B. subtilis*, and in particular the bioFDB gene cassette.

9 Claims, 4 Drawing Sheets

SEQUENCE LISTING

<160> NUMBER OF SEQ ID NOS: 5

<210> SEQ ID NO 1
<211> LENGTH: 3156
<212> TYPE: DNA
<213> ORGANISM: Bacillus subtilis

<400> SEQUENCE: 1

| | | | | | |
|---|---|---|---|---|---|
| ggatccacga | ggttacgagc | cttgaagatt | gattcctggt | taaacgagcg | gttagacaga | 60 |
| atgaaagaag | ccggcgtaca | tcgtaacctg | cggtcaatgg | atggagcgcc | ggttccagag | 120 |
| aggaatattg | atggcgaaaa | tcaaacggtc | tggtcctcaa | acaattattt | agggctcgca | 180 |
| agcgatagac | gtttgatcga | tgcagcccaa | acagcattgc | agcaatttgg | gacaggaagc | 240 |
| agcggttcac | gtttaacgac | aggcaattcg | gtctggcatg | aaaagctaga | aaagaagatt | 300 |
| gccagcttta | aactgacaga | agcggccctg | ctgttttcga | gcggttactt | ggccaatgtc | 360 |
| ggtgtccttt | catccttgcc | agaaaaggaa | gatgtcattt | taagtgacca | gctcaatcat | 420 |
| gcaagtatga | tcgacggctg | ccgactttct | aaggctgata | cagttgttta | tcggcatatt | 480 |
| gatatgaatg | atcttgaaaa | caagctgaat | gaaacacagc | gttatcagcg | ccgtttatc | 540 |
| gtaacagacg | gagtattcag | catggatggc | acaatcgccc | ctcttgatca | gatcatctca | 600 |
| cttgcgaaac | gctatcatgc | cttcgtggtc | gttgatgatg | cccacgcaac | aggagttttg | 660 |
| ggcgattcgg | gacaaggaac | gagtgaatac | tttggtgttt | gtcccgacat | tgttatcggc | 720 |
| accttaagca | aagctgttgg | cgcggaagga | ggttttgcgg | caggatcagc | ggtcttcatc | 780 |
| gacttttgc | tgaaccatgc | cagaacattt | atctttcaaa | ccgctattcc | gccagccagc | 840 |
| tgtgcggctg | ctcacgaggc | tttcaacatc | attgaagcca | gcaggaaaa | acgacagctt | 900 |
| ttattttctt | atatcagcat | gatcagaacc | agtctgaaga | atatgggtta | tgtggtgaaa | 960 |
| ggagatcaca | caccgattat | tcctgtagtc | attggcgatg | cccataaaac | ggtcctattt | 1020 |
| gctgaaaaac | tgcagggcaa | gggaatttat | gctcctgcca | ttcggccgcc | aaccgttgcg | 1080 |
| ccgggtgaaa | gccggattcg | aagcttgggc | agcaggtcga | gatcagggaa | tgagtttata | 1140 |
| aaataaaaaa | agcacctgaa | aaggtgtctt | tttttgatgg | ttttgaactt | gttctttctt | 1200 |
| atcttgatac | atatagaaat | aacgtcattt | ttattttat | tttagttgct | gaaaggtgcg | 1260 |
| ttgaagtgtt | ggtatgtatg | tgttttaaag | tattgaaaac | ccttaaaatt | ggttgcacag | 1320 |
| aaaaacccca | tctgttaaag | ttataagtga | ctaaacaaat | aactaaatag | atgggggttt | 1380 |
| cttttaatat | tatgtgtcct | aatagtagca | tttattcaga | tgaaaaatca | agggttttag | 1440 |
| tggacaagac | aaaaagtgga | aaagtgagac | catgtgctta | ggaagacgag | ttattaatag | 1500 |
| ctgaataaga | acggtgctct | ccaaatattc | ttatttagaa | aagcaaatct | aaaattatct | 1560 |
| gaaaagggaa | tgagaatagt | gaatggacca | ataataatga | ctagagaaga | aagaatgaag | 1620 |
| attgttcatg | aaattaagga | acgaatattg | gataaatatg | gggatgatgt | taaggctatt | 1680 |
| ggtgtttatg | gctctcttgg | tcgtcagact | gatgggccct | attcggatat | tgagatgatg | 1740 |
| tgtgtcatgt | caacagagga | agcagagttc | agccatgaat | ggacaaccgg | tgagtggaag | 1800 |
| gtggaagtga | attttgatag | cgaagagatt | ctactagatt | atgcatctca | ggtggaatca | 1860 |
| gattggccgc | ttacacatgg | tcaattttc | tctattttgc | cgatttatga | ttcaggtgga | 1920 |
| tacttagaga | aagtgtatca | aactgctaaa | tcggtagaag | cccaaacgtt | ccacgatgcg | 1980 |
| atttgtgccc | ttatcgtaga | agagctgttt | gaatatgcag | gcaaatggcg | taatattcgt | 2040 |

-continued

```
gtgcaaggac cgacaacatt tctaccatcc ttgactgtac aggtagcaat ggcaggtgcc      2100
atgttgattg gtctgcatca tcgcatctgt tatacgacga gcgcttcggt cttaactgaa      2160
gcagttaagc aatcagatct tccttcaggt tatgaccatc tgtgccagtt cgtaatgtct      2220
ggtcaacttt ccgactctga gaaacttctg gaatcgctag agaatttctg gaatgggatt      2280
caggagtgga cagaacgaca cggatatata gtggatgtgt caaaacgcat accattttga      2340
attcgaaagc gccgattgag tcttaccgga tggtgaataa ggaaacgctg cttgaaggcg      2400
cgaagcgggc gcacgatctg aatatcggca catattgtat cgtggcaagc ggcagaggtc      2460
cgtctaacag agaagtggat caggtcgtag atgcggttca ggaaattaaa gagacgtatg      2520
gactgaagat ttgtgcatgt cttggactgt gaagccaga gcaggcgaag cggctcaaag       2580
atgcaggagt agaccgctat aatcataatt tgaatacgtc acagagaaac cattcaaaca      2640
tcacaacctc acatacatac gatgacagag tcaatacggt tgaaatcgca aaagaatcgg      2700
ggctgtctcc gtgttcaggc gccattatcg ggatgaagga gacgaaacag gatgtcattg      2760
acatcgccaa aagcttgaag gctcttgacg cggattccat tcctgtgaat tttttgcatg      2820
caattgatgg cacgccgtta gaaggcgtca acgaattaaa cccgctgtat tgtttaaaag      2880
tgctggcgct gttccgtttt atcaatccat caaaagaaat tcgcatttcc ggaggaagag      2940
aggtcaatct ccgcacattg cagccattag ggctttacgc cgcaaactcc attttttgtcg     3000 gagactactt aacaactgcc gggcaagagg agacggagga tcataaaatg ctgagtgatt      3060
taggctttga agttaatca gtcgaagaaa tgaaggctag tttaagtgcg aaaagctgaa       3120
agaatcaata aaagcaatcg gtatgatgtc gaattc                                3156
```

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer
      Sequence BioF+1

<400> SEQUENCE: 2
gagaggatcc acgaggttac gagc                                             24

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Primer
      Sequence BioB-1

<400> SEQUENCE: 3
gcgacgaatt cgacatcata ccgattgc                                         28

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer
      Sequence pBESTBstBI+1

<400> SEQUENCE: 4
gcgcttcgaa gcttgggcag caggtcg                                          27

```
-continued

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Primer
      Sequence pBESTBstBI-1

<400> SEQUENCE: 5
gcgcttcgaa ttcaaaatgg tatgcg                                              26
```

POLYNUCLEOTIDE PORTIONS OF THE BIOTIN OPERON FROM B. SUBTILIS FOR USE IN ENHANCED FERMENTATION

FIELD OF THE INVENTION

The present invention relates to a process for producing a target fermentation product. More particularly, the present invention relates to a process for over-producing a target fermentation product in a microorganism having a mutation which causes auxotrophic growth of the microorganism, but that does not compromise its ability to over-produce the target fermentation product. Host cells and polynucleotide sequences used in the process are also provided.

BACKGROUND OF THE INVENTION

Many commercially valuable products are produced by fermentation reactions. For example, riboflavin, which is an essential vitamin that is required by all bacteria, animals, and plants, is synthesized by plants and bacteria, however, it cannot be produced by higher animals, which must acquire it from their diet.

Riboflavin is produced commercially for use as a food and feed additive by, for example, fermentation reactions using *Ashbya govsypii*, *Eremothecium ashbyii*, or *Candida flareri* cells. (See e.g., Ainsworth, G. C. and Sussman, A. S., The Fungi, Academic Press, New York (1965); Heefner, D. L., et al., WO 88/09822; Hickey, R. J., Production of Riboflavin by Fermentation, in Industrial Fermentation (Underkofler, L. A. and Hickey, R. J., eds.) pp. 157–190, Chemical Publishing Co., New York (1954); and Perlman, D., et al., Fermentation Ind. Eng. Chem. 44:1996–2001 (1952).

The enzymes required to catalyze the biosynthesis of riboflavin from guanosine triphosphate (GTP) and ribulose-5-phosphate are encoded by four genes (ribG, ribB, ribA, and ribH) in *B. subtilis*. See, FIG. 1A. These genes are located in an operon, the gene order of which differs from the order of the enzymatic reactions catalyzed by the enzymes. For example, GTP cyclohydrolase II, which catalyzes the first step in riboflavin biosynthesis is encoded by the third gene in the operon, ribA. See, FIG. 2. The ribA protein also encodes a second enzymatic activity, i.e., DHB synthase, which catalyzes the conversion of ribulose-5-phosphate to the four-carbon unit DHB. Deaminase and reductase are encoded by the first gene of the operon, ribG. The bi-functionality of the ribA and ribG gene products may facilitate a coordinated riboflavin precursor flux. The penultimate step in riboflavin biosynthesis is catalyzed by lumazine (Lum) synthase, the product of the last rib gene, ribH. Riboflavin synthase, which controls the last step of the pathway, is encoded by the second gene of the operon, ribB. The function of the gene X (FIG. 1) located at the 3' end of the rib operon is, at present, unclear, however, its gene product is not required for riboflavin synthesis.

Transcription of the riboflavin operon from the ribP$_1$ promoter is controlled by an attenuation mechanism involving a regulatory leader region located between ribP$_1$ and ribG. RibO mutations within this leader region result in deregulated expression of the riboflavin operon. Deregulated expression is also observed in strains containing missense mutations in the ribC gene. The ribC gene has recently been shown to encode the flavin kinase/FAD synthase of *B. subtilis*. See, Mack, M., et al., *J. Bact.*, 180:950–55 (1998). Deregulating mutations reduce the flavokinase activity of the ribC gene product resulting in reduced intracellular concentrations of flavinmononucleotide (FMN), the effector molecule of the riboflavin regulatory system.

Recently, a *Bacillus subtilis* microorganism was genetically engineered to produce high yields of riboflavin during a short fermentation cycle. See, Perkins, J. B., U.S. Pat. No. 5,837,528 ("Perkins '528"), which is hereby incorporated by reference as if recited in full herein. This approach combined classical genetic mutant selection and fermentation improvement with genetic engineering of the riboflavin biosynthetic genes by deregulating and increasing the level of gene expression. In this system, the expression of the rib genes was increased by mutating the flavokinase encoding ribC gene, by linking the rib genes to strong, constitutive promoters, and by increasing the copy number of the rib genes.

For example, in the engineered rib operon present in plasmid pRF69 disclosed by Perkins '528, the entire ribP$_1$ promoter and most of the regulatory leader region were deleted and replaced with a constitutive phage SPO1promoter, P$_{15}$. See, FIG. 1B. In addition, the phage promoter was introduced between the ribB and ribA genes to further increase the transcription of the corresponding downstream genes. Finally, pRF69 was provided with a chloramphenicol resistance gene downstream of the rib genes. pRF69 was targeted by single cross-over transformation into the rib operon of the host microorganism RB50, which contained mutations deregulating purine biosynthesis and which contained a mutation in the ribC gene deregulating riboflavin biosynthesis.

The genomic structure resulting from single crossover transformation of RB50 with pRF69 includes a chloramphenicol resistance gene flanked by the wild type rib operon at one end and by the engineered rib operon of pRF69 at the other end. The iterative elements within this structure originate increased copy numbers of the resistance gene and of the flanking rib operon upon selection of the pRF69 transformed bacteria for increased chloramphenicol resistance.

Enhanced transcription of the rib genes in RB50 containing multiple (n) copies of the modified rib operon of pRF69 (i.e., RB50::[pRF69]$_n$) has been confirmed by Northern blot analysis. Unlike wild-type *B. subtilis*, which accumulated very small amounts of RNA transcript that covered the entire rib operon, RB50::[pRF69]$_n$ accumulated large amounts of shorter transcripts that covered primarily the first two genes of the operon. The second P$_{15}$ promoter engineered upstream of ribA gave rise to significant accumulation of RNA transcripts that covered the three downstream genes of the rib operon. See, Perkins, J. B., et al., *J. Ind. Microbiol Biotechnol.*, 22:8–18 (1999).

In a riboflavin fed batch fermentation reactor containing, for example, *B. subtilis* RB50::[pRF69]$_n$, biomass and riboflavin are produced from a common fermentation substrate, glucose. The rate by which glucose is pumped into the reactor ("glucose feeding rate") is critical to its utilization in the production of biomass and riboflavin, respectively. A fast glucose feeding rate allows the culture to grow at elevated rates causing an excess of biomass formation and a reduction of the riboflavin yield. Glucose feeding rates that are too slow, however, while lowering biomass production, result in low riboflavin productivity. Because low yield, low productivity, or both increase riboflavin production costs, a balance must be struck between biomass and riboflavin production by carefully regulating the glucose feeding rate in commercial riboflavin fermentation reactors.

SUMMARY OF THE INVENTION

In view of the deficiencies noted above, it would be desirable to optimize production of a target fermentation product, such as riboflavin, while concurrently maintaining biomass production at a level that is most efficient for the size and type of reactor used.

One embodiment of the present invention is a process for producing a target fermentation product. This process includes providing a fermentation medium containing a recombinantly-produced microorganism that over-produces a target fermentation product and that contains a mutation which causes auxotrophic growth of the microorganism, wherein the auxotrophy within the microorganism does not compromise the ability of the microorganism to produce the target fermentation product. The medium is then supplied with all substrates required for production of the fermentation product, a substrate for the target fermentation product, and a substrate complementing the auxotrophy. The former substrate(s) is/are provided in excess, ensuring maximal productivity. The latter substrate (i.e., substrate complementing the auxotrophy) is supplied in limited amounts to maintain biomass formation at a low rate.

Another embodiment of the present invention is a process for decoupling production of a target fermentation product from biomass production in a fermentation medium. This process includes providing a recombinantly produced microorganism that has been engineered to contain a polynucleotide sequence which encodes the biosynthetic enzymes for a target fermentation product. In this process, the maximal production of the target fermentation product is dependent on an unlimited supply of a target fermentation product substrate for the microorganism. Next, an auxotrophy is introduced into the microorganism to control biomass production by limiting the concentration of a substrate complementing the auxotrophy in the fermentation medium. A fermentation production microorganism made by the process set forth above is also provided.

The present invention also includes as a further embodiment a polynucleotide, which is selected from SEQ ID NO:1, an auxotrophy-introducing homolog or fragment of SEQ ID NO:1, or a polynucleotide sequence containing an insertion, deletion, or substitution of SEQ ID NO:1, which polynucleotide retains the ability to cause an auxotrophy in a host cell.

Another embodiment of the present invention is a host cell transformed with a polynucleotide sequence including SEQ ID NO:1, a homolog or a fragment of SEQ ID NO:1 which retains its ability to cause an auxotrophy in the host cell, or a polynucleotide sequence containing an insertion, deletion, or substitution of SEQ ID NO:1, which polynucleotide retains the ability to cause an auxotrophy in the host cell.

The present invention also provides as another embodiment a riboflavin production microorganism RB50 containing multiple copies of the engineered rib operon pRF69 and transformed with the polynucleotide sequence SEQ ID NO:1.

DETAILED DESCRIPTION OF THE INVENTION

Figure 1A:
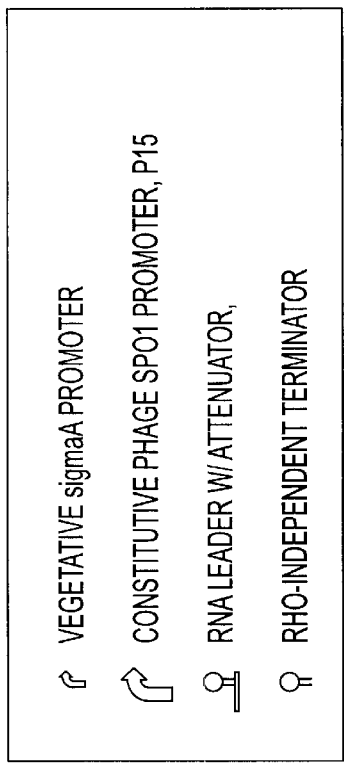
FIG. 1 shows the *B. subtilis* wild type riboflavin operon and the engineered rib operon of pRF69 in accordance with the present invention. (A) shows the location of the ribO regulatory site and the structural genes, ribG, ribB, ribA, and ribH, and gene X. The upstream sigma A promoter $ribP_1$ and the putative internal promoter $ribP_2$ are marked. The rho-independent transcription terminator downstream of gene X and the transcription attenuator upstream of ribG are depicted as well. (B) shows the structure of the engineered rib operon of pRF69 with the location of the DNA sequences containing the constitutive phage SPO1 promoter, $P_{15}$.
Figure 1A:
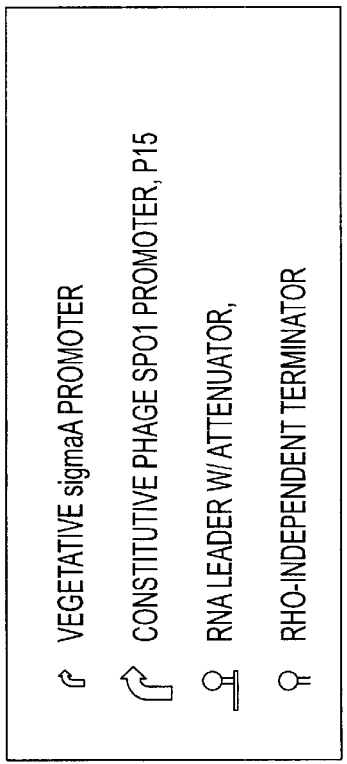
Figure 1B:
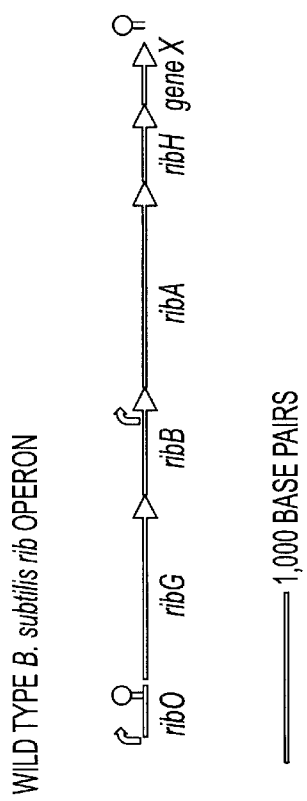
Figure 1B:
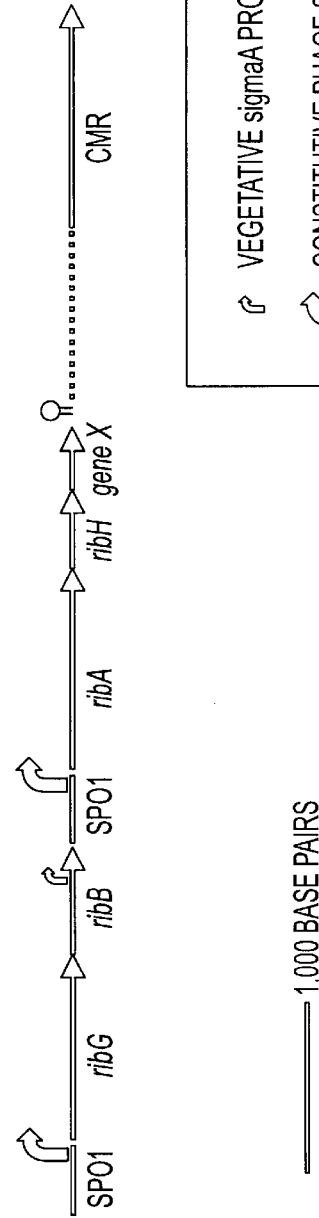
Figure 2:
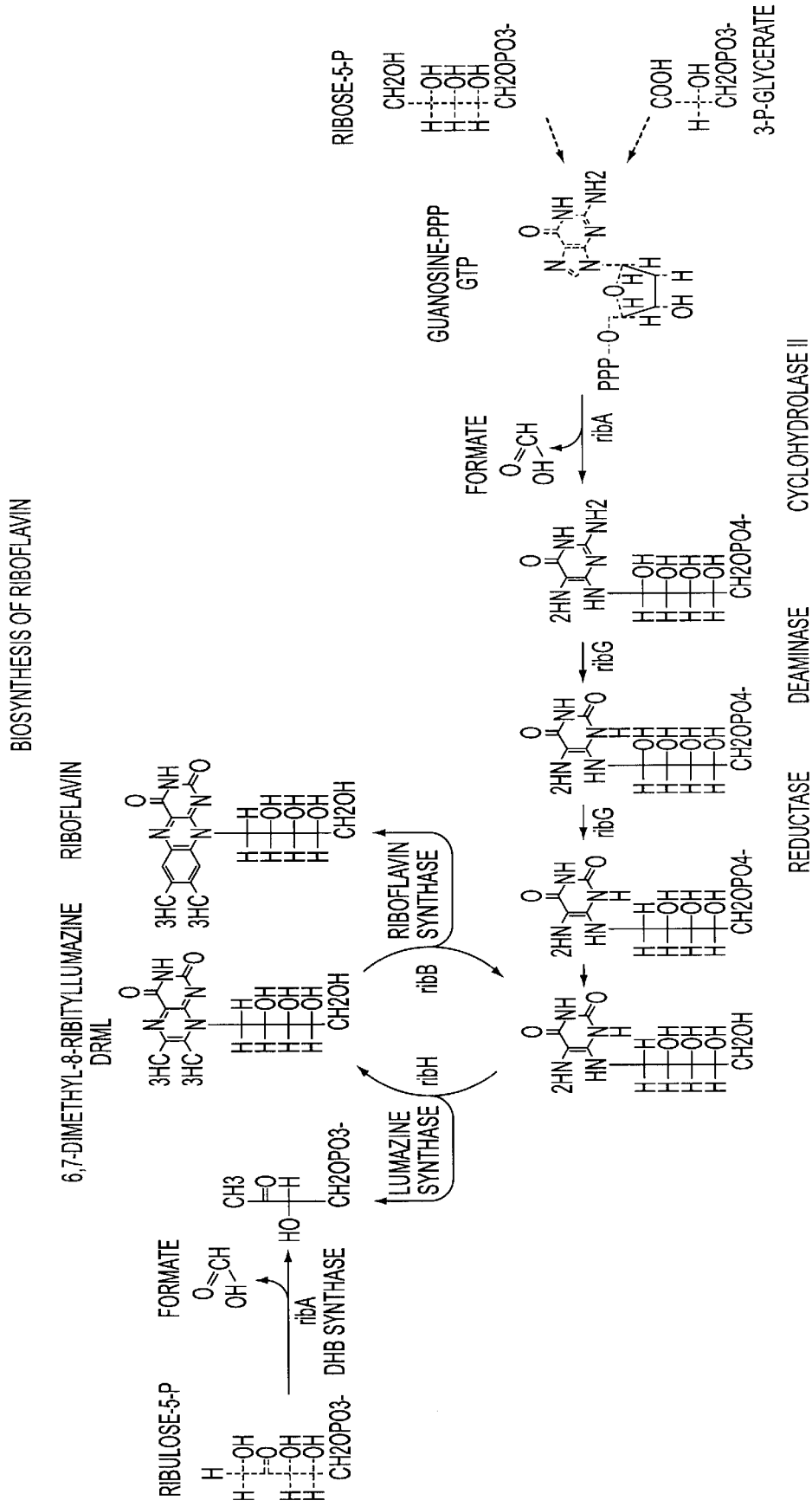
FIG. 2 shows the riboflavin biosynthetic pathway of *B. subtilis*.

The present invention includes a process for producing a target fermentation product. In this process, a fermentation medium is provided containing a recombinantly produced microorganism that over-produces a target fermentation product. The microorganism also contains a mutation that causes auxotrophic growth of the microorganism, wherein the auxotrophy does not compromise the ability of the microorganism to produce the fermentation product.

As used herein, the phrase "recombinantly-produced microorganism" means any microorganism modified by recombinant DNA techniques to produce commercially useful target fermentation products, such as for example, riboflavin. For example, a microorganism according to the present invention may include bacterial cells. The microorganism may be selected from Escherichia, Bacillus, Cyanobacter, Streptomyces, and Corynebacteria cells. Preferably, the microorganism is selected from *E. coli, B. subtilis, B. amyloliquefaciens, B. lichiniformis, C. glutamicum*, or *B. ammoniagenes*.

In the present invention, the microorganism is modified using recombinant DNA techniques to increase production of the target fermentation product above wild type production levels as set forth in more detail in the examples. As used herein, "target fermentation product" means a compound produced by fermentation, such as for example riboflavin, pantothenic acid, biotin, thiamin, folic acid, pyridoxine, and amino acids.

For example, when the target fermentation product is riboflavin, the recombinantly-produced microorganism is a *B. subtilis* cell, such as for example, the *B. subtilis* production microorganism designated as RB50::[pRF69]$_n$ containing multiple (n) copies (for example about 5 to about 20 copies) of pRF69 encoding a rib operon modified with the strong phage SPO1promoter ($P_{15}$) to enhance transcription of the rib genes. This recombinantly-produced microorganism produces significantly more riboflavin than wild type microorganisms. See, Perkins '528.

The *Bacillus subtilis* microorganism RB50 used in the present invention was deposited with the Agricultural Research Culture Collection (NRRL), 1815 North University Street, Peoria, Ill. 61604, USA, under the terms of the Budapest Treaty on May 23, 1989, and was assigned accession number B 18502. Plasmid pRF69 used in the present invention was deposited with the American Type Culture Collection, 12301 Parklawn Dr., Rockville, Md. 20852, USA, on Jun. 6, 1990, and was assigned accession number ATCC 68338.

In the present invention, the recombinantly-produced microorganism contains a mutation that causes auxotrophic growth. As used herein the term "mutation" refers to an alteration in the genomic sequence of the microorganism, which may be introduced by any convenient means including, for example, chemical and UV mutagenesis, followed by screening or selection for a desired phenotype, construction of dysfunctional genes in vitro by recombinant techniques used to replace the intact counterparts of the genes in the genome of the microorganism, by single and double cross-over recombinations, and other well known techniques. See, Sambrook, et al., Molecular Cloning, A Laboratory Manual, 2nd Ed., Cold Spring Harbor Laboratory Press (1989) and, Harwood and Cutting, Molecular Biology Methods For Bacillus, John Wiley and Sons (1990), pp. 27–74.

The terms "auxotroph," "auxotrophic," and "auxotrophy" are used interchangeably herein and refer to a microorganism that has been modified, by e.g. a mutation, to require the addition of an exogenous compound to grow, that prior to the mutation, the microorganism could produce itself. Thus, "auxotrophic growth" refers to the ability of a microorganism that has been rendered auxotrophic for a particular substrate to grow in a defined fermentation media.

The exogenous compound required for auxotrophic growth is referred to herein as "a substrate complementing the auxotrophy" or "the complementing substrate." Examples of a substrate complementing the auxotrophy in the present invention include amino acids, nucleotides, and vitamins. In the present invention, a microorganism may be an auxotroph for biotin, tryptophan, lysine, and/or adenine. The microorganism may also be engineered to contain more than one such auxotrophy. The selection of a particular auxotrophy is not critical to the present invention, so long as the auxotrophy decouples production of a target fermentation product from biomass production and the auxotrophy does not compromise the ability of the microorganism to produce the target fermentation product.

In certain microorganisms used in fermentation reactors, such as *B. subtilis*, various substrates are used as sources for carbon, nitrogen, and oxygen. Such substrates are required to produce both the target fermentation product, as well as the biomass. Auxotrophic microorganisms also require a supply of "complementing" substrates as set forth above.

The phrase "maximal productivity" as used herein means the maximum amount of a target fermentation product that a microorganism is able to produce when all substrates required or beneficial for target fermentation product formation (e.g., sources for carbon, oxygen, nitrogen, etc.) are available in excess, at given chemo-physical parameters, such as pH and temperature. Maximal productivity is measured by: gm product produced/gm Biomass/hr.

The phrase "maximal growth rate" as used herein means the highest growth rate that is achieved by a microorganism when provided with an excess of all substrates required for growth at given chemo-physical parameters, such as pH and temperature. Thus, the maximal growth rate of a microorganism is the amount of relative increase of the microorganism's biomass per time. Maximal growth rate and maximal productivity of a microorganism may be determined by those skilled in the art using, e.g., continuous culture fermentations.

If one of the substrates required for production of the fermentation product is not provided in excess, this substrate will become the production rate limiting substrate and its supply will determine the rate by which the target fermentation product is produced (i.e., the productivity of the process). Likewise, if one of the substrates required for growth of the biomass is not provided in excess, this substrate will become the growth limiting substrate and its supply will determine the growth rate.

Biomass and target fermentation product production are said to be "coupled" if the limited supply of a substrate determines both the growth rate of the biomass and the productivity for the. target fermentation product. In a coupled process, the same substrate is the limiting substrate for growth and production. For a riboflavin fermentation system, glucose is used by the microorganism as the major carbon source required for biomass and product formation. Glucose limitation will result in a "coupled" process. An increase or decrease in the rate that glucose is supplied to the fermentor (and thus the microorganism) determines whether both riboflavin and biomass production are up- or downregulated, respectively.

Biomass and target fermentation product production are said to be "decoupled" if the limited supply of one substrate (substrate 1) determines the growth rate of the microorganism, whereas the supply of another substrate (substrate 2) determines the productivity for the target fermentation product. In a decoupled process, the unlimited supply of substrate 2 will result in maximal productivity of the microorganism. Thus, in a decoupled process, such as for example, one using an auxotrophic microorganism of the present invention, glucose (substrate 2) may be supplied to a fermentation reactor at a non-limiting rate to achieve maximal productivity of the target fermentation product, whereas the substrate complementing the auxotrophy (substrate 1) is supplied to the fermentation reactor at a rate that prevents the biomass from increasing at its maximal growth rate and thus limits biomass production.

The presence of an auxotrophy in a microorganism according to the present invention and the growth limiting supply of the corresponding substrate complementing the auxotrophy must not compromise the ability of the microorganism to produce the target fermentation product. In the present invention, an auxotrophy "compromises" the microorganism's ability to produce the target fermentation product if the limited supply of the substrate complementing the auxotrophy results in less than 50% of maximal productivity for the target fermentation product. The productivity of the target fermentation product is also said to be "compromised" by the auxotrophy if the maximal productivity of a production microorganism carrying that auxotrophy is less than 50% of the maximal productivity of an otherwise identical microorganism lacking the auxotrophy.

In the present invention, the presence of an auxotrophy in a microorganism is confirmed by determining biomass production in a suitable fermentation medium in the presence or absence of the corresponding substrate complementing the auxotrophy. See, Example 1. As used herein, "biomass production" or "biomass growth" means the ability of a particular microorganism to grow and divide. In the present invention, biomass production is determined by standard microbiology methods, such as for example, by weighting the total cell dry mass or by measuring the turbidity of a fermentation sample at a particular wavelength between, e.g., 550–660 nm. See, Example 3. Alternatively, the ability of a microorganism to grow and divide, i.e., produce biomass, may be assessed by colony formation on an agar plate.

Where applicable, the presence of a mutation in the genome of a microorganism leading to an auxotrophy may be confirmed by standard molecular biology techniques, such as for example Southern hybridization, PCR (as in Example 1), or DNA sequencing. Such techniques are readily available to one skilled in the art. See, for example, chpts. 8–14 of Sambrook, et al., Molecular Cloning, A Laboratory Manual, 2nd Ed., Cold Spring Harbor Laboratory Press (1989) and chpt. 15 of Ausubel et al. Eds., Current Protocols in Molecular Biology, John Wiley and Sons, Inc. (1998).

Figure 3:
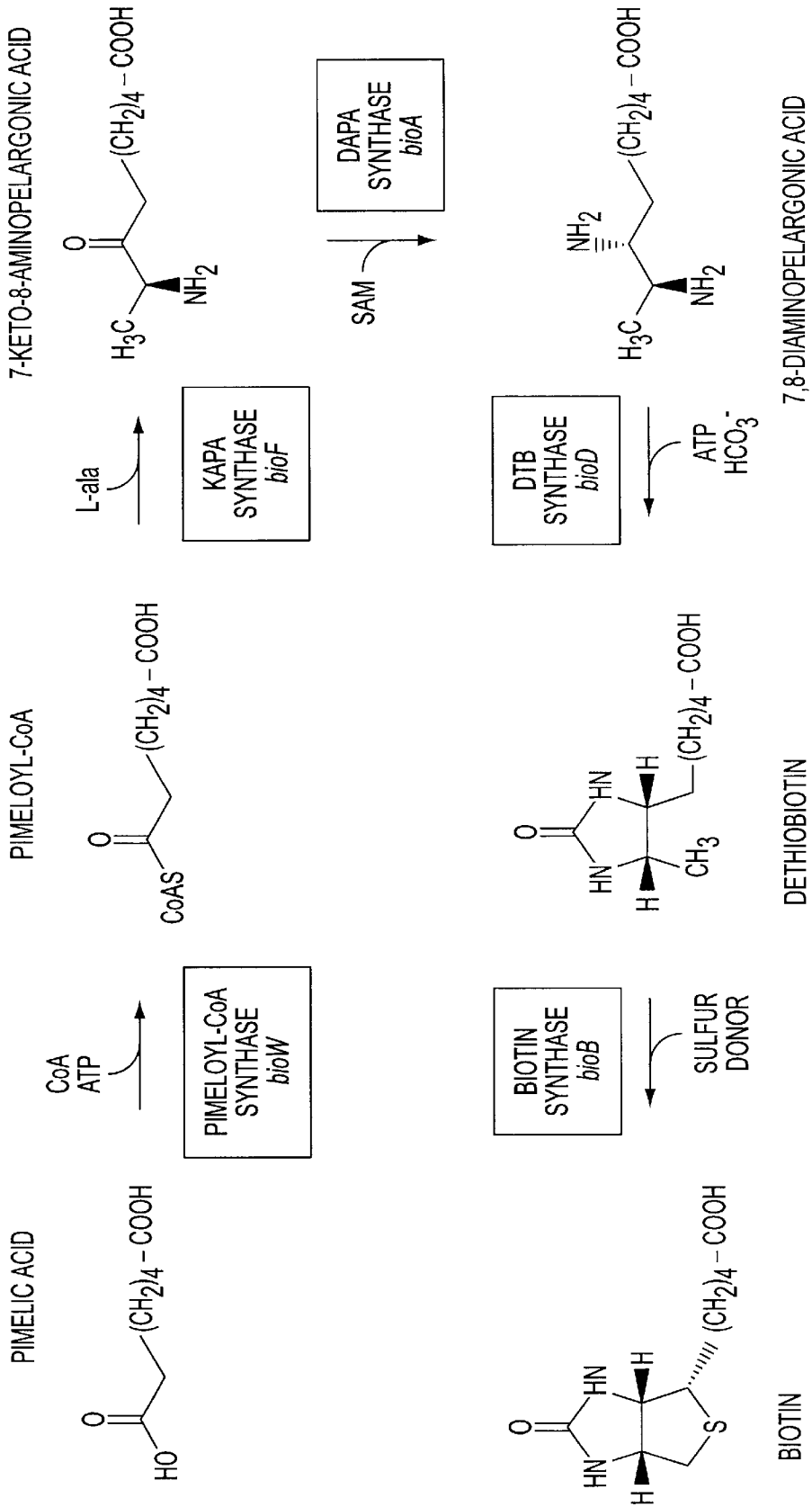
FIG. 3 shows the biotin biosynthesis pathway of Bacillus.
Figure 4:
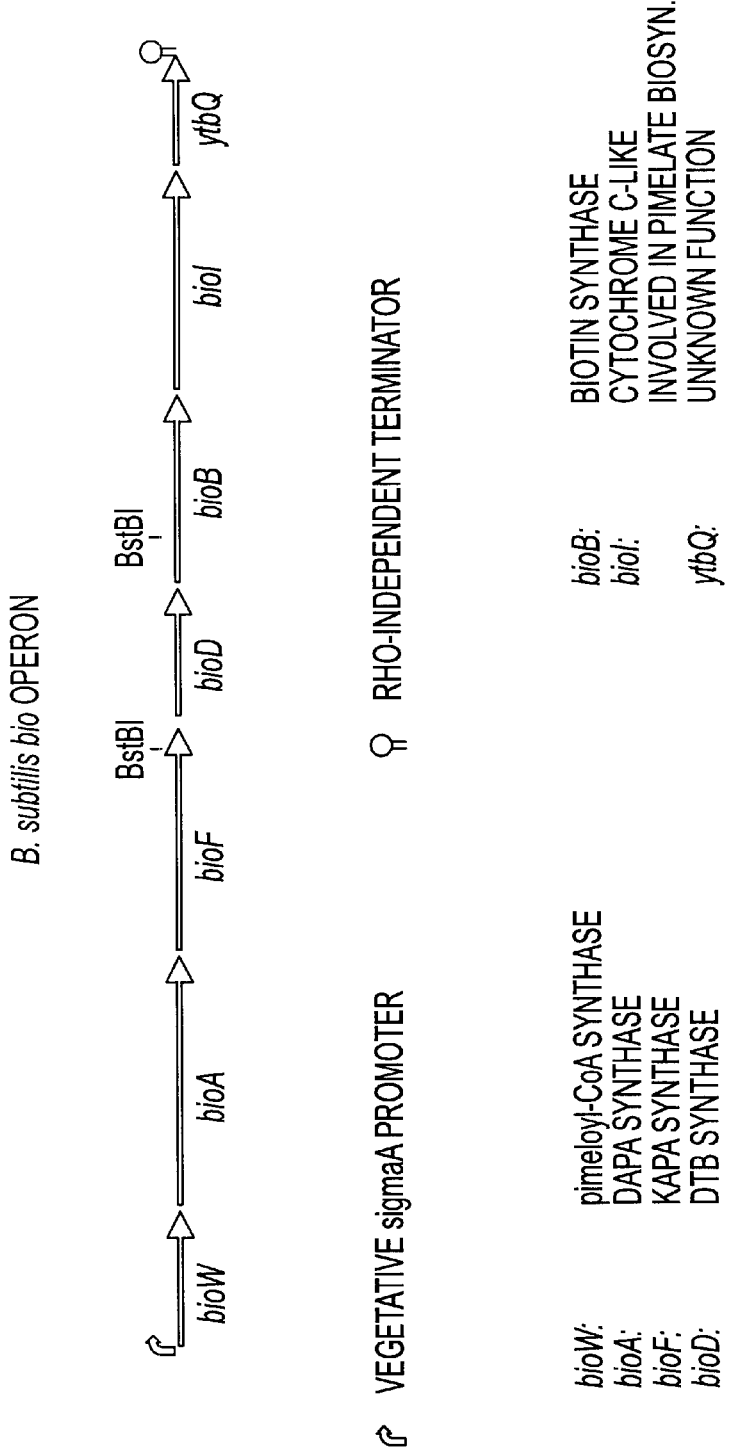
FIG. 4 shows the biotin (bio) biosynthetic operon of *B. subtilis*.

As set forth above, a microorganism according to the present invention preferably is a biotin auxotroph. Biotin or vitamin $B_8$ is required as a prosthetic group for a number of enzymes including pyruvate carboxylase and acetyl CoA carboxylase. Biotin is bio-synthesized from pimelic acid involving a number of enzymatic steps. See, FIG. 3. Genes for biotin synthesis are clustered in a single operon in *B. subtilis*. See, FIG. 4. A microorganism that is an auxotroph for biotin is unable to grow without supplementation with biotin, i.e., the substrate complementing the auxotroph. In a similar manner, cells that are lysine, tryptophan, and adenine auxotrophs are likewise unable to grow without supplementation of the fermentation medium with the respective substrate complementing the auxotroph.

In commercial fermentation processes, it is desirable to limit the growth rate of biomass to, e.g., reduce the consumption of costly fermentation substrates and to keep the oxygen demand and the heat development of the metabolically active biomass within the limits of the fermentation reactor's oxygen transfer and cooling capacities. In a "coupled" process, limitation of biomass production through limiting the supply of a target fermentation substrate will reduce the productivity of the microorganism for the target fermentation product. In a "decoupled" process using an auxotrophic microorganism according to the present invention, biomass production may be limited by restricting the supply of the substrate complementing the auxotrophy, whereas the target fermentation product is produced at the microorganism's maximal productivity for that product because all substrates required for product formation are provided in excess.

In the present invention, decoupling target fermentation product production from biomass production is accomplished by introducing an auxotrophy into a microorganism that has already been modifed to over-express a target fermentation product, e.g. riboflavin. Thus, in the present invention, maximal production of the target fermentation product is achieved when the microorganism is synthesizing the target fermentation product at its maximal productivity.

Accordingly, the auxotrophic microorganism of the present invention is cultured in a fermentation medium containing a substrate complementing the auxotroph at a concentration sufficient to maintain biomass at a defined growth rate. All other substrates required by the microorganism are supplied to the fermentation medium at concentrations that do not limit the ability of the microorganism to produce the target fermentation product at its maximal productivity.

The particular concentrations of the substrate complementing the auxotroph and of the other substrates required to achieve maximal productivity for the target fermentation product that are in or supplied to the fermentation medium will vary depending on the particular auxotrophy selected, the target fermentation product, the reactor used, the production microorganism, and other well known fermentation variables. For example, in a riboflavin production culture containing a production microorganism auxotrophic for biotin, the amount of glucose (i.e.,. the target fermentation substrate) added to the fermentation medium must be sufficient to over-produce riboflavin (i.e., the target fermentation product). As used herein, the term "over-produce" means that the microorganism produces the target fermentation product from a substrate that is used as a carbon source above at least 0. 1% (w/w) yield, preferably above 1% (w/w) yield, such as for example, above 4% (w/w) yield.

In the present invention, the ratio of the concentration of the substrate for the target fermentation product to the substrate complementing the auxotrophy in the fermentation medium is from about 1:10,000,000 to about 1:10, preferably from about 1:1,000,000 to about 1:100.

In the present invention, the target fermentation product may be isolated from the microorganism and/or the medium. As used herein, the term "isolated" means that the target fermentation product is purified, or at least partially purified. The target fermentation product may be purified by methods known in the art. Such methods include for example, filtration, centrifugation, and/or extraction. The target fermentation product may be further purified by re-crystallization from aqueous or organic solvents or applying other methods known in the art, such as for example, ion-exchange, size-exclusion, or hydrophobic interaction chromatography. For a detailed description of procedures for riboflavin isolation and purification from a fermentation broth, see Kupfer E., EP 730034 A1.

In a preferred embodiment, a recombinantly produced microorganism that over-produces riboflavin is produced. This microorganism is further modified to contain a biotin auxotrophy that decouples riboflavin production from biomass production. Thus, the substrate complementing the auxotroph is biotin and the substrate for the fermentation product is glucose. For example, a microorganism according to the present invention is the *B. subtilis* riboflavin production microorganism RB50 containing multiple copies of the engineered rib operon pRF69. See, Perkins '528. In this embodiment, a biotin auxotrophy is introduced into RB50 cells containing the engineered rib operon pRF69, which decouples riboflavin production from biomass production. This biotin auxotrophic riboflavin production microorganism is designated as RB50::[pRF69] Bio. When cultivated with biotin as the growth limiting substrate, the specific riboflavin productivity of this strain is enhanced about three-fold compared to a glucose limited culture. See, Example 3.

The present invention also includes derivatives of RB50::[pRF69] Bio. As used herein, a "derivative" of RB50::[pRF69] Bio is any *B. subtilis* cell which contains the engineered rib operon of pRF69 or a polynucleotide sequence that is at least 25% identical to the engineered rib operon of pRF69, preferably at least 50% identical to the engineered rib operon of pRF69, and that is a biotin auxotroph, such as for example, other Bacillus microorganisms with recombinantly engineered rib operons in which riboflavin production is decoupled from biomass production. In the present invention, the percent identity of the polynucleotide sequences are determined using the BLAST program and the server at the National Center of Biotechnology Information (Bethesda, Md., USA).

In the present invention, the microorganism may contain first a polynucleotide sequence coding for one or more polypeptides with enzymatic activities for producing riboflavin and one or more transcription elements which are not naturally associated with, but which are now transcriptionally linked to this polynucleotide sequence.

As used herein, "transcription element" includes enhancers, promoters, natural or synthetic ribosomal binding sites, and/or terminators as are known to those of skill in the art. See, Perkins '528. In the present invention, the polynucleotide sequence may contain more than one transcription element as set forth above. Preferably, the polynucleotide sequence includes at least one promoter.

The present invention also includes a process for decoupling production of a target fermentation product from biomass production in a fermentation medium. This process includes providing a recombinantly produced microorganism that has been engineered to contain a polynucleotide sequence which encodes the biosynthetic enzymes for a target fermentation product, the maximal production of which is dependent upon an unlimited supply of a substrate for the target fermentation product. An auxotrophy is then introduced within the microorganism to control biomass production by limiting the concentration of a substrate complementing the auxotrophy in the fermentation medium.

For purposes of the present invention, the auxotrophy is "introduced" into the microorganism using any convenient means. For example, the auxotrophy may be introduced into the microorganism using classical mutagenesis techniques, as well as, recombinant biological techniques. Preferably, a polynucleotide sequence that encodes a defective gene or a set of defective genes, whose intact counterparts within the microorganism are required to produce an essential compound for biomass production, is introduced into the microorganism by transformation.

The term "transformation" as used herein refers to the introduction of the polynucleotide sequence into a microorganism and the recombination of the polynucleotide sequence with the genomic DNA of the microorganism by a single or double cross-over mechanism thereby replacing the corresponding intact gene or set of genes. See, Harwood and Cutting, Molecular Biology Methods For Bacillus, John Wiley and Sons (1990), pp. 27–74. Introduction of the polynucleotide sequence into the microorganism may be achieved by any convenient means well-known to those skilled in the art, such as for example, transformation of linearized or circular polynucleotide sequences into natural competent recipient cells or protoblasts, generalized transduction, transfection, lipofection, electroporation, particle bombardment, and the like. See, Id. and Sambrook et al., Molecular Cloning A Laboratory Manual (2nd Ed.) Cold Spring Harbor Laboratory Press (1989).

The polynucleotide sequence of the present invention may contain deletion-insertion mutations within a bioFDB gene cassette of *Bacillus subtilis* as set forth in more detail in the Examples. Preferably, the polynucleotide sequence is SEQ ID NO:1. In the present invention, SEQ ID NO:1 may be modified at its 3'- and 5' ends with extension sequences, each of which are several hundred base pairs in length, to increase the transformation efficiency of SEQ ID NO:1. The extension sequences are random sequences, which should be less than 80% homologous to DNA sequences of the recipient cells to prevent recombination at undesired loci. Such a polynucleotide sequence is then used to transform a microorganism capable of over-producing a target fermentation product.

Transformants positive for the deletion-insertion mutation, i.e., which are auxotrophs, are selected using standard selection protocols. See, Id. For example, the polynucleotide sequence used to transform the microorganism may include various selection markers, including for example antibiotic resistance markers, color producing markers, etc. Preferably, the marker is a neomycin resistance marker, and selection for the desired transformation includes identifying microorganisms capable of growing in fermentation media supplemented with neomycin, and which overproduce the target fermentation product, such as riboflavin, as set forth in more detail in Example 1.

In another embodiment of the present invention, a polynucleotide sequence is provided. *Bacillus subtilis* or a closely related species, e.g., *Bacillus amyloliquefaciens* or *Bacillus lichiniformis* are made auxotrophic for biotin upon transformation with this polynucleotide sequence.

Preferably, the polynucleotide sequence is SEQ ID NO:1 or an auxotrophy-introducing homolog of SEQ ID NO:1. Preferably, a Bacillus host cell is transformed with SEQ ID NO:1, or an auxotrophy-introducing homolog thereof, which retains its ability to cause an auxotrophy in a host cell.

In the present invention, a polynucleotide is considered an "auxotrophy-introducing homolog" of SEQ ID NO:1 if the polynucleotide contains sequences that are more than 70% identical to the partial bioF and bioB sequences present within SEQ ID NO:1 as determined using BLAST.

The present invention also includes host cells transformed with a polynucleotide sequence containing SEQ ID NO:1 or a homolog of SEQ ID NO:1, which causes an auxotrophy in the host cell, or a polynucleotide sequence containing one or more insertions, deletions, and/or substitutions of SEQ ID NO:1, which sequence retains the ability to cause an auxotrophy in the host cell.

The host cell may be any microorganism capable of producing a target fermentation product according to the present invention. For example, the host cell may be selected from Escherichia, Bacillus, Cyanobacter, Streptomyces, and Corynebacteria cells. Preferably, the microorganism is selected from *E. coli*, *B. subtilis*, *B. amyloliquefaciens*, *B. lichiniformis*, *C. glutamicum*, or *B. ammoniagenes*. More preferably, the host cell is a *B. subtilis* cell, such as for example RB50 containing multiple copies of the engineered rib operon pRF69.

The following examples are set forth to illustrate the processes and compositions of the present invention. These examples are illustrative only and are not intended to limit the scope of the invention in any way. For example, the present invention may be varied by carrying out a decoupled process in large scale industrial fermentors, varying the dilution rate from 0.3 1/h to 0.001 1/hour, increasing the concentration of the components in the fermentation medium, increasing glucose concentration up to 400 g/l, and carrying out a decoupled process according to the present invention in a batch or fed batch fermentation reactor. The media components for all of these variations, including biotin, would be determined and adjusted by one skilled in the art.

EXAMPLES

Example 1

Construction of *Bacillus subtilis* Auxotrophic Mutants

In the following examples, a biotin auxotrophy-introducing polynucleotide sequence was first constructed in *E. coli*. Transformation of a natural competent *B. subtilis* microorganism with the polynucleotide sequence resulted in a biotin auxotrophic *B. subtilis* mutant. A PBS1 phage lysate prepared from this mutant was then used to introduce the auxotrophy, via generalized transduction, into the production microorganism RB50 containing multiple copies of the engineered rib operon pRF69. Standard recombinant DNA techniques were used for the construction of the polynucleotide sequence and the *Bacillus subtilis* mutants. See, for example, Sambrook et al., Molecular Cloning A Laboratory Manual (2nd Ed.) Cold Spring Harbor Laboratory Press (1989) and Harwood and Cutting, Molecular Biology Methods For Bacillus, John Wiley and Sons (1990).

A. Construction of a Biotin Auxotroph.

To construct a bioFDB deletion-insertion mutation, a 2938 bp DNA fragment containing the complete bioF, bioD, and bioB genes, was amplified by PCR using genomic DNA from *B. subtilis* microorganism 1012 (Saito et al., Mol.Gen-.Genet. 170:117–122 (1979)) as a template and primers BioF+1(5'- GAGAGGATCCACGAGGTTACGAGC-3') (SEQ ID NO:2) and BioB-1 (5'-GCGACGAATTCGACATCATACCGATTGC-3') (SEQ ID NO:3). The reaction conditions for the PCR reaction consisted of 25 cycles of denaturation at 95° C. for 1 minute, annealing at 55° C. for 1minute, and extension at 72° C. for 3 minutes. The PCR product was purified using the Wizard PCR purification kit (Promega Corp.) and was doubly-digested with BamHI and EcoRI. The digested PCR product was cloned into (1) a BamHI-EcoRI-digested pUC19, resulting in plasmid pNMR3 and into (2) a BamHI-EcoRI-digested pBluescriptII SK+, resulting in plasmid pNMR4.

The 1.2-kb neomycin-resistance cassette from plasmid pBEST501 (Itaya et al., Nucleic Acid Res. 17:4410(1989)) was amplified using primers pBESTBstBI+1 (5'-GCGCTTCGAAGCTTGGGCAGCAGGTCG-3') (SEQ ID NO:4) and pBESTBstBI-1 (5'-GCGCTTCGAATTCAAAATGGTATGCG-3') (SEQ ID NO:5) in a PCR reaction consisting of 25 cycles of denaturation at 95° C. for 1minute, annealing at 55° C. for 1minute, and extension at 72° C. for 3 minutes. Both pNMR3 and pNMR4 were digested with BstBI which removed 1019 bp, encompassing parts of the bioF and bioB genes and the entire bioD gene. The amplified neomycin-resistant cassette was purified and digested with BstBI, and was cloned into BstBI-digested pNMR3 and pNMR4.

The following plasmids were then created: pNMR5, containing the neomycin-resistant cassette inserted into the bioFDB genes in the same orientation as bio transcription in pUC19; pNMR6 containing the neomycin-resistant cassette inserted into the bioFDB genes in the opposite orientation to bio transcription in pUC19;and pNMR7 containing the neomycin-resistant cassette inserted into bioFDB genes in the opposite orientation as bio transcription in pBluescriptII SK+. All three plasmids were linearized with XbaI and transformed into natural competent *B. subtilis* 1012 cells. Transformants were selected on TBAB plates containing neomycin at a final concentration of 5 $\mu$g ml$^{-1}$. Approximately 250 transformants were observed, from which 30 were patched onto Spizen's Minimal Medium in the presence or absence of 0.1 mg ml$^{-1}$ biotin. 23 of 30 colonies were auxotrophic for biotin. 6 colonies were analyzed by PCR analysis of the fusion junctions, and 2 clones (designated *B. sublilis* NM1and NM2, respectively) were kept for further use.

*B. subtilis* microorganism NM2 was used as a donor microorganism for preparation of PBS1phage lysate. This lysate was used to transduce the riboflavin production microorganism RB50 provided with the modified riboflavin operon pRF69. RB50 refers to the host microorganism of *B. subtilis*, which contains several mutations introduced to improve production of nucleotides and riboflavin. pRF69 refers to a rib operon modified by the introduction of strong phage promoters which was introduced at the rib locus of pRF50. The modified operon pRF69 was amplified to high copy numbers. A detailed description of the microorganism RB50 and the modified rib operon pRF69 is presented in Perkins '528. A number of neomycin-resistant colonies were obtained which were unable to grow on Spizen's Minimal Medium in the absence of exogenous biotin. Three of these clones were analyzed by PCR and Southern hybridization, and were shown to contain the bioFDB::neo mutation. One of these clones designated NM9 was selected and renamed RB50::[pRF69]Bio$^-$. Southern blot hybridization revealed the presence of pRF69.

RB50::[pRF69]Bio$^-$ was cultivated in a rich, complex medium (VY medium, DSMZ Medium 577) supplemented with 10 $\mu$g/ml chloramphenicol to an optical density OD 660=1. One milliliter of this broth was transferred into 20 ml VY medium supplemented with 30 $\mu$g/ml chloramphenicol and after reaching OD 1, again 1 ml of culture was transferred into 20 ml VY medium supplemented with 60 $\mu$g/ml chloramphenicol. The same passage was repeated using VY containing 80 $\mu$g/ml chloramphenicol. After reaching an OD of 1, this culture was supplemented with 15% (Vol/Vol) glycerol and 1 ml aliquots were frozen at −80° C. The stepwise increase in the antibiotic concentration was used to select for bacteria with increased copy number of the modified rib operon pRF69. See Perkins '528.

Example 2

Continuous Culture Fermentations

Decoupling of growth and production was achieved and resulted in the desired positive effect on the riboflavin productivity of RB50::[pRF69]Bio$^-$ as described in detail below using continuous chemostat cultures. According to standard textbooks, see e.g. Neidhardt, et al., Physiology Of The Bacterial Cell, Sinauer Associates, Inc. (1990), the growth rate of the cells within a continuous fermentation culture, which has reached steady state conditions (chemostat), equals the dilution rate at which the fermentor is operated. The concentration of the biomass within such a fermentor is correlated to the concentration of the rate limiting substrate.

Fermentations were carried out in New Brunswick bioreactors Model Bioflow 3000 (3 l total volume) equipped with blade stirrers. Continuous chemostat cultivation was used with an inlet pump that controlled the flow rate and an overflow that controlled the liquid level in the reactor. The fermentation variables were set as follows:

| | | | |
|---|---|---|---|
| Liquid volume: | 1200 ml | Dilution rate: | 0.15 |
| Temperature: | 37° C. | pH: | 6.75 |
| Aeration: | 1 l/min compressed air | Stirrer speed: | 1000 rpm |

The dissolved oxygen concentration was at every stage of the cultivation above 20% of air saturation.

The fermentation medium used in the batch phase and as feeding medium contained the following components at the given final concentrations: 0.25 g/l Na-glutamate, 1.57 g/l KH$_2$PO$_4$, 1.57 g/l K$_2$HPO$_4$, 2.74 g/l Na$_2$HPO$_4$.12 H$_2$O, 4.00 g/l NH$_4$Cl, 0.1 g/l citric acid, 6.80 g/l (NH$_4$)$_2$SO$_4$, 22 g/l Glucose.H$_2$O, 0.2 ml/l Antifoam (Silicon based), 14.1 mg/l FeSO$_4$.7 H$_2$O; 10.5 mg/l CaCl$_2$.2 H$_2$O, 9.4 mg/l MnSO$_4$.1 H$_2$O, 2.7 mg/l CoCl$_2$.6 H$_2$O, 1.0 mg/l (NH$_4$)$_6$HMo$_7$ O$_{24}$.4 H$_2$O, 0.67 mg/l AlCl$_3$.6 H$_2$O, 0.50 mg/l CUCl$_2$.2 H$_2$O; 6.7 g/l MgSO$_4$.7 H$_2$O, 2.68 mg/l ZnSO$_4$.7 H$_2$O.

Na-glutamate, KH$_2$PO$_4$, K$_2$HPO$_4$, Na$_2$HPO$_4$.12 H$_2$O, NH$_4$Cl, citric acid, and (NH$_4$)$_2$SO$_4$ were dissolved in 85% of the end volume, the pH was adjusted to pH 4 by adding hydrochloric acid and the solution was autoclaved. Glucose was dissolved in 10% of the end volume and autoclaved separately. Antifoam was autoclaved separately as a concentrate. The FeSO$_4$.7 H$_2$O solution was prepared freshly as a 500 fold concentrate for each batch of medium and sterilized by filtration. The other salts were prepared as 500 fold concentrates and sterilized by filtration in the following groups: group1: CaCl$_2$.2 H$_2$O ; group 2: MnSO$_4$. 1H$_2$O, CoCl$_2$.6 H$_2$O, (NH$_4$)$_6$HMo$_7$O$_{24}$.4 H$_2$O, AlCl$_3$.6 H$_2$O, CuCl$_2$.2 H$_2$O; group 3: MgSO$_4$.7 H$_2$O, ZnSO$_4$.7 H$_2$O. The separately sterilized solutions were combined under sterile conditions and sterile water was added in order to reach the final volume.

The fermentors were inoculated with 40 ml of a seed culture prepared as follows: One aliquot of the frozen RB50::[pRF69]Bio$^-$ bacterial suspension of example 1 was thawed and transferred into 100 ml VY medium supplemented with 60 μg/ml chloramphenicol. The culture was incubated at 37° C. until reaching OD=1(typically after 12 to 15 hours).

The batch phase of the fermentation, i.e. the phase during which the glucose in the fermentation medium was used up by the growing bacteria, lasted for about 24 hours. After glucose depletion was reached as indicated by a sharp rise in the dissolved oxygen value, the fermentations were switched to continuous mode (start of the inlet and outlet pumps) at a dilution rate of 0.15 per hour. The fermentation media, that were administered to the fermentors, were the media described above (containing 20 g/l glucose) complemented with either 10 μg/l biotin (fermentation A of example 3) or 3 μg/l biotin (fermentation B of example 3). Fermentation samples were taken and analyzed after the cultures had reached the steady state, i.e. after the fermentor volume had been exchanged more than 5 times.

Example 3

Biomass and Riboflavin Production in Coupled and Decoupled Processes

20 μl of 40% NaOH solution was added to a 1ml fermentation sample of example 2 immediately after collection from the fermentation reactor. The sample was incubated for 20 seconds at room temperature to dissolve riboflavin crystals within the sample. An aliquot of this suspension was diluted and neutralized with 0.1 molar potassium phosphate buffer pH 7.0. Biomass content in the suspension was measured by determination of the turbidity at 660 nm. The dilution of the sample was adjusted to achieve readings between 0.05 and 0.3 absorption units.

As a confirmation, the biomass content in the suspension was determined by weighting the dry cell mass. A 1ml aliquot of the suspension obtained from above was transferred into pre-weighed Eppendorf vials and the bacteria were collected by centrifugation (14,000 rpm, 5 minutes). The bacteria were washed once with 1ml deionized water and dried in vacuo at 80° C. until constancy of weight was achieved. The dry cell mass was determined gravimetrically.

The riboflavin concentration was determined by HPLC analysis from a cell free supernatant of the suspension obtained from above. A Hewlett-Packard 1100 System equipped with a binary pump, a column thermostat and a diode array detector was used. The sample was fractionated over a stainless-steel Supelcosil LC-8-DB column (150×4.6 mm, 3 μm particle size). A gradient elution of solvent A (4 mmol/l sulfuric acid solution in water) and solvent B (methanol) according to the following time profile was used:

| Time [min] | % A | % B |
|---|---|---|
| 0 | 94 | 6 |
| 2 | 94 | 6 |
| 15 | 50 | 50 |
| 20 | 50 | 50 |

The column temperature was set to 20° C., and the flow rate was 1.0 ml/minute. The UV absorption was recorded at 280 nm and the riboflavin peak was detected at about 11 minutes (total run time 20 minutes). The riboflavin concentrations were calculated by comparing the integrated peak of the sample to those of riboflavin standards (Sigma, St. Louis, Mo., USA).

The results of the fermentation runs described in example 2 are summarized in Table 1 (values represent the means obtained from 3 samples taken between 45 hours and 71 hours after start of the continuous mode):

TABLE 1

| | fermentation A coupled process (10 μg/l biotin, 20 g/l glucose) | fermentation B decoupled process (3 μg/l biotin, 20 g/l glucose) |
|---|---|---|
| biomass concentration g/l | 5.87 +/− 0.19 | 3.36 +/− 0.18 |
| riboflavin concentration g/l | 0.608 +/− 0.033 | 0.802 +/− 0.044 |
| biomass yield on glucose % | 29.4 +/− 1.0 | 17.0 +/− 0.9 |
| riboflavin yield on glucose % | 3.04 +/− 0.17 | 4.05 +/− 0.16 |
| biomass productivity g riboflavin/g biomass * hour | 0.0154 +/− 0.0009 | 0.0354 +/− 0.0030 |

In fermentation B (Table 1) with 3 μg/l biotin and 20 g/l glucose in the fermentation medium 3.36 g/l biomass were produced. Upon increase of biotin to 10 μg/l while keeping glucose at 20 g/l biomass production increased to 5.87 g/l biomass (fermentation A, Table 1). Further increase of the biotin supply did not result in higher biomass production. Thus, in fermentation A glucose (the fermentation substrate) is the growth limiting substrate. In fermentation B glucose is supplied at a non growth-limiting rate. Rather, biotin. (the complementing substrate) limits biomass growth. Hence, fermentations A and B of Table 1 represent coupled and decoupled processes as defined herein, respectively.

The results of this example show further that in a decoupled process with biotin as the growth limiting substrate and glucose as the fermentation substrate (fermentation B), the productivity of the biomass is significantly increased (3-fold) over a coupled process (fermentation A). In addition, the product yield, i.e. the amount of riboflavin produced on consumed glucose is 33% higher in the decoupled process compared to the coupled process.

The invention being thus described, it will be obvious that the same may be varied in many ways. Such variations are not to be regarded as a departure from the spirit and scope of the invention and all such modifications are intended to be included within the scope of the following claims.

What is claimed is:

1. An isolated polynucleotide sequence comprising SEQ ID NO:1.

2. An isolated polynucleotide sequence according to claim 1 consisting of SEQ ID NO:1.

3. A vector comprising the polynucleotide sequence of claim 1.

4. A vector according to claim 3 wherein the vector is a plasmid.

5. A host cell containing the vector of claim 3.

6. A host cell according to claim 5 wherein the host cell is a *B. subtilis* cell.

7. A host cell transformed with a polynucleotide sequence according to claim 1.

8. A host cell according to claim 7 wherein the host cell is a *B. subtilis* cell.

9. A riboflavin production microorganism RB50 containing multiple copies of pRF69, which microorganism is transformed with the polynucleotide sequence of SEQ ID NO:1.

* * * * *